US008858420B2

(12) United States Patent
Elofsson

(10) Patent No.: US 8,858,420 B2
(45) Date of Patent: Oct. 14, 2014

(54) VIBRATION SENSOR FOR BONE CONDUCTION HEARING PROSTHESIS

(75) Inventor: Rasmus Elofsson, San Francisco, CA (US)

(73) Assignee: Cochlear Limited, Macquarie University, NSW (AU)

( * ) Notice: Subject to any disclaimer, the term of this patent is extended or adjusted under 35 U.S.C. 154(b) by 218 days.

(21) Appl. No.: 13/421,810

(22) Filed: Mar. 15, 2012

(65) Prior Publication Data

US 2013/0245362 A1 Sep. 19, 2013

(51) Int. Cl.
*A61F 11/04* (2006.01)
*H04R 25/00* (2006.01)

(52) U.S. Cl.
USPC .............................................. 600/25; 381/60

(58) Field of Classification Search
USPC .............................. 600/25; 381/312-331, 60
See application file for complete search history.

(56) References Cited

U.S. PATENT DOCUMENTS 5,984,859 A * 11/1999 Lesinski ........................ 600/25
2004/0175005 A1* 9/2004 Roeck ............................ 381/74
2007/0167671 A1* 7/2007 Miller, III ....................... 600/25
2009/0097681 A1* 4/2009 Puria et al. .................... 381/318
2009/0136050 A1 5/2009 Hakansson

OTHER PUBLICATIONS

Hakansson, Bo et al., "Skull Simulator for Direct Bone Conduction Hearing Devices" Scand Audiol 18: 91-98, 1989.
BAHA Listener, for daily testing of a BAHA by a carer/parent. Convenans Limited, BPIFMG81, Dec. 2005.

* cited by examiner

*Primary Examiner* — Christine Matthews
*Assistant Examiner* — Joshua D Lannu
(74) *Attorney, Agent, or Firm* — McDonnell Boehnen Hulbert & Berghoff LLP

(57) ABSTRACT

The present application discloses a vibration-based hearing prosthesis configured to measure the vibration applied by a hearing prosthesis to the skull of the hearing prosthesis recipient while the recipient is wearing the hearing prosthesis. Directly measuring the applied vibration in situ allows hearing characteristics to be more accurately mapped to voltage inputs. A recipient's hearing threshold and associated voltage input may be directly measured. Additionally, measuring the applied vibrations allows co-listening. A doctor can monitor the sound output from a vibration-based hearing prosthesis as it is worn by a recipient. Directly measuring the vibration output also allows an additional degree of freedom in diagnostics because a recipient can perform diagnostic tests at home.

28 Claims, 9 Drawing Sheets

VIBRATION SENSOR FOR BONE CONDUCTION HEARING PROSTHESIS

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea, where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids may include bone anchored hearing aids, direct acoustic cochlear stimulation devices, or other vibration-based devices.

A bone anchored hearing aid typically utilizes a surgically-implanted mechanism to transmit sound via direct vibrations of an implant recipient's skull. An external component of the vibration-based hearing aid detects sound waves, which are converted into a series of electrical stimulation signals delivered to the implant recipient's skull bones via an electromechanical transducer (e.g., a mechanical actuator). By providing a stimulation to the recipient's skull, the bone anchored hearing aid enables the recipient's middle ear and auditory canal to be bypassed, which is advantageous for recipients with medical conditions that affect the middle or outer ear. The vibrations of the recipient's skull bones cause fluid motion within the recipient's cochlea, thereby enabling the recipient to perceive sound based on the vibrations. Similarly, a direct acoustic cochlear stimulation device typically utilizes a surgically-implanted mechanism to transmit sound via direct vibrations of the cochlea. Other non-surgical vibration-based hearing aids may use similar vibration mechanisms to transmit sound via direct vibration of a recipient's teeth or other cranial or facial bones.

SUMMARY

The present application discloses systems and methods for use with a vibration-based hearing prosthesis. The vibration-based hearing prosthesis disclosed herein is configured with a vibration sensor connected in serial in the pathway between a transducer in the hearing prosthesis and a recipient of the prosthesis. The present systems and methods allow the output vibration created by a vibration-based hearing aid to be measured in situ (i.e., while a recipient is wearing the vibration-based hearing aid). Thus, the output from the vibration driver can be directly measured while the hearing prosthesis is in an operating mode connected to a recipient. Measuring the vibration output by the hearing prosthesis in situ enables a more accurate mapping of a patient's hearing threshold in terms of an applied vibration stimulus.

With traditional systems, a hearing professional typically tests and configures a vibration-based hearing prosthesis on a human skull simulator before being fitted to a recipient. A skull simulator is a device used to simulate the acoustical properties of an average human's skull. However, hearing prosthesis measurements conducted with a skull simulator do not always accurately simulate the operation of the hearing prosthesis with respect to a specific prosthesis recipient. The present systems and methods enable direct measurements of the stimulation provided to a hearing prosthesis recipient from a vibration-based hearing prosthesis. Directly measuring the stimulation with a vibration sensor in situ provides both a more precise measurement and removes the need for a skull simulator.

DETAILED DESCRIPTION

Figure 1:
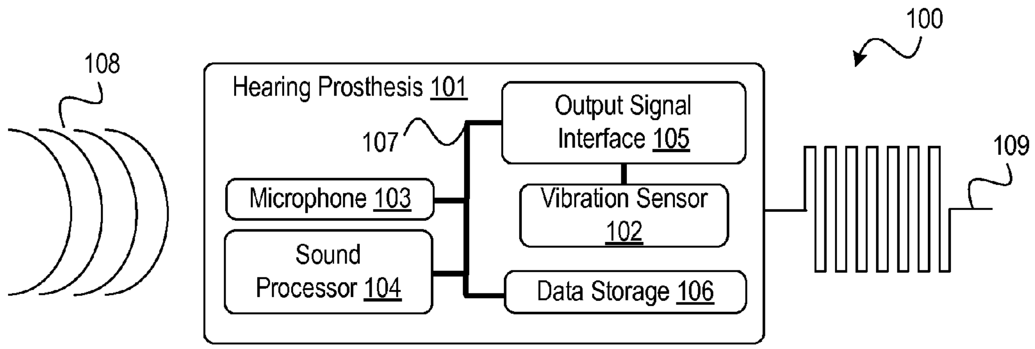
FIG. 1 shows one example of a hearing prosthesis with a vibration sensor.

FIG. 1 shows one example of a hearing prosthesis 101 with an integrated vibration sensor 102 configured according to some embodiments of the disclosed systems, methods, and articles of manufacture. The hearing prosthesis 101 may be a bone anchored hearing aid or other vibration-based hearing prosthesis, or any other type of hearing prosthesis configured to receive and process at least one signal from an audio transducer (such as microphone 103) of the prosthesis and create a mechanical vibration output.

Figure 2:
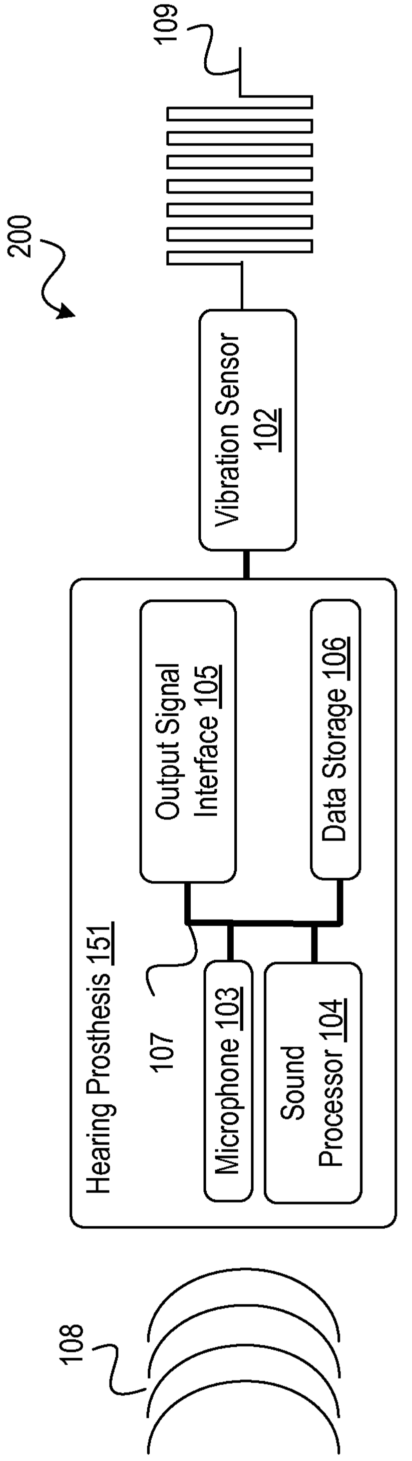
FIG. 2 shows one example of a hearing prosthesis connected to a vibration sensor.

The hearing prosthesis 101 includes a vibration sensor 102, a microphone 103, a sound processor 104, an output signal interface 105, and data storage 106, all of which are connected directly or indirectly via circuitry 107. In other embodiments, the hearing prosthesis 101 may have additional or fewer components than the prosthesis shown in FIG. 1. For example, hearing prosthesis 151 as shown in FIG. 2 has similar components to hearing prosthesis 101, except the vibration sensor 102 is mounted external to the hearing prosthesis 151. The term hearing prosthesis used herein applies to a hearing prosthesis either with or without a vibration sensor mounted internally.

Additionally, the components may be arranged differently than shown in FIG. 1. For example, depending on the type and design of the hearing prosthesis, the illustrated components may be enclosed within a single operational unit or distributed across multiple operational units (e.g., an external unit, an internal unit, etc.). Similarly, in some embodiments, the hearing prosthesis 101 may additionally include one or more processors (not shown) configured to determine various settings for the sound processor 104. The various settings for the sound processor 104 may be stored in data storage 106.

The microphone 103 receives acoustic signals 108, and the sound processor 104 analyzes and encodes the acoustic signals 108 into electrical signals that are converted to output signals for application to a recipient via the output signal interface 105. For a vibration-based hearing prosthesis, the output signal interface 105 is an electromechanical transducer (e.g., a mechanical actuator) and the output signals are mechanical vibration signals. The electromechanical transducer converts the electrical signal from the sound processor 104 to the mechanical vibration signals 109 that are applied to the recipient. In operation, electrical signals supplied to the electromechanical transducer cause the transducer to generate mechanical vibration signals 109 that are proportional to the electrical signals.

In some embodiments, a recipient has a medical bone-anchored implant mounted into his or her skull, through a process known as osseointegration. In some embodiments, the bone-anchored implant is made of titanium and is mounted directly in the skull bone of the recipient. In these embodiments, the hearing prosthesis attaches to the bone-anchored implant and directly vibrates the skull via the bone-anchored implant.

The vibrations generated by the bone-anchored implant are conducted by the skull bones to the cochlea in the inner ear. If a recipient has conductive hearing loss (i.e., a hearing loss due to an issue in either the outer ear or middle ear) the pathway for sound transmission through the ear to the cochlea may not be functioning correctly. The mechanical vibration signals 109 generated by the hearing prosthesis cause fluid motion in the recipient's cochlea. And the fluid motion in the cochlea causes the recipient to experience sound sensations corresponding to the sound waves received by the microphone 103 and encoded by the processor 104.

FIG. 1 shows a hearing prosthesis 101 that has an integrated vibration sensor 102. Conversely, FIG. 2 shows an embodiment where the vibration sensor may be added to a hearing prosthesis 151 that does not have a built-in or integrated vibration sensing capability. In some embodiments, the output signal interface 105 is connected to a vibration sensor 102 within the hearing prosthesis 101, as shown in FIG. 1. In another embodiment, as shown in FIG. 2, a hearing prosthesis is connected to a vibration sensor 102 external to the hearing prosthesis 151. Regardless of the position of the vibration sensor 102, either mounted inside hearing prosthesis 101 or outside, the functionality is similar. Mechanical vibration signals generated by the output signal interface 105 and applied to the recipient can be measured by the vibration sensor 102.

The vibration sensor 102 may be a piezo-electric element, a piezo-resistive element, or other vibration sensor. A piezo-electric element generates a time-varying voltage in response to a mechanical stress, such as a mechanical vibration signal. The time-varying voltage output will generally be in proportion to the mechanical stress applied. For example if a mechanical vibration signal applied to the piezo-electric element has a frequency of 500 Hertz (Hz), the output of the piezo-electric element will be a time-varying voltage that has a frequency of approximately 500 Hz. If the amplitude of the mechanical vibration signal applied to the piezo-electric element is increased, the time-varying voltage output of the piezo-electric element will increase in a generally linear fashion. Thus, measuring the time-varying voltage output of the piezo-electric element enables measurement and characterization of mechanical vibration signals applied to the recipient.

A piezo-resistive element generates a change in resistance in response to a mechanical stress, such as a mechanical vibration sensor. A piezo-resistive element behaves similar to the piezo-electric element previously described, except that the resistance of the piezo-resistive element varies over time rather than the voltage. In particular, the time-varying resistance of the piezo-resistive element will have substantially the same frequency and amplitude as an applied mechanical vibration signal. Thus, measuring the time-varying output resistance of the piezo-resistive element enables measurement and characterization of mechanical vibration signals applied to the recipient.

Both piezo-electric and piezo-resistive elements may be made relatively small. Example piezo-electric and piezo-resistive elements may be as small as a few millimeters. Thus, the addition of either a piezo-electric or piezo-resistive element will not substantially affect the form factor of a hearing prosthesis. For example, the size and shape of hearing prosthesis may not change, or only change slightly, to incorporate either a piezo-electric and piezo-resistive element. Either type of piezo element may be used with the methods, apparatuses, and systems herein. Additionally, other vibration sensors not specifically mentioned herein can be configured to work with the system as well. Further, due to the reciprocal nature of piezo elements, the piezo elements can also cause vibrations in the systems described herein. For example, if a voltage is applied to the terminals of a piezo element, it will vibrate. Thus, piezo elements may be used to both create the stimulus as well as measure the stimulus.

Figure 3A:
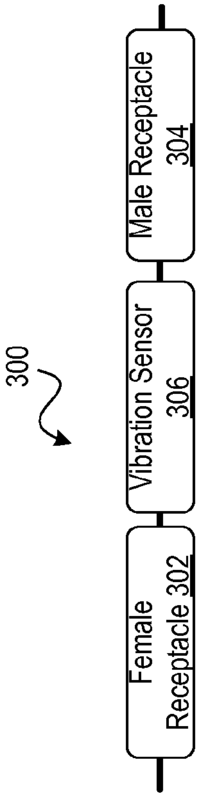
FIG. 3A shows an example vibration sensor for use with a vibration-based hearing prosthesis.

FIG. 3A shows a vibration sensor unit 300. The vibration sensor unit 300 has a vibration sensor 306 similar to the one shown in FIG. 2. The vibration sensor unit 300 of FIG. 3A may be coupled between a vibration-based hearing prosthesis and a recipient of the hearing prosthesis. In embodiments where the recipient has a bone-anchored implant, the bone-anchored implant will have a coupling to which the hearing prosthesis can connect. One type of example coupling may be a mechanical coupling featuring a female receptacle 302 into which a male receptacle 304 is inserted. In various embodiments, the male and female receptacles and may be mechanical couplings, magnetic couplings, or other type of coupling. Example mechanical couplings include snap couplings, bayonet couplings and screw couplings, additional types of mechanical couplings may be used as well.

Vibration sensor unit 300 as shown in FIG. 3A has a vibration sensor 306 that is connected to both a female receptacle 302 and a male receptacle 304. The vibration sensor unit 300 is placed between a vibration-based hearing prosthesis and the prosthesis recipient. An example vibration sensor unit 300, like the one shown in FIG. 3, may measure approximately 6 mm in length. Other configurations and dimensions can be used as well.

Figure 3B:
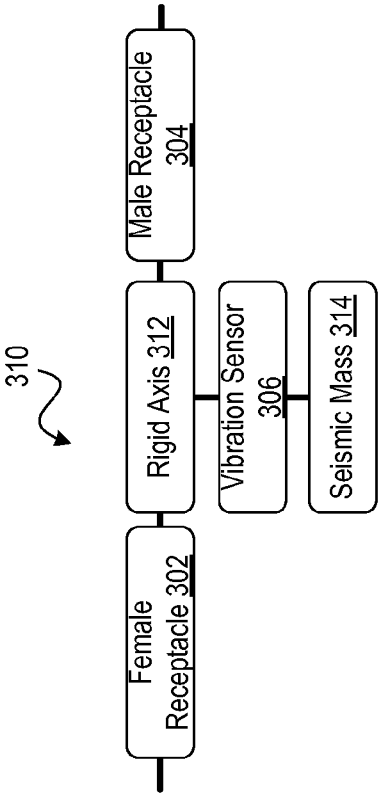
FIG. 3B shows an example vibration sensor for use with a vibration-based hearing prosthesis.

FIG. 3B shows a vibration sensor unit 310. The vibration sensor unit 310 has a vibration sensor 306 similar to the one shown in FIG. 2 and FIG. 3A. The vibration sensor unit 310 of FIG. 3B may be coupled between a vibration-based hearing prosthesis and a recipient of the hearing prosthesis, similar to the vibration sensor unit 310 described with respect to FIG. 3A. Vibration sensor unit 310 as shown in FIG. 3B has a rigid axis 312 that is connected to both a female receptacle 302 and a male receptacle 304. The vibration sensor 306 is affixed to the rigid axis 312. The vibration sensor 306 measures a vibration or acceleration conducted by the rigid axis 312. Additionally, vibration sensor unit 310 has a seismic mass 314 affixed to the vibration sensor. The seismic mass 314 can be configured to adjust the output signal from the vibration sensor 306. For example, the seismic mass 314 may tune the vibration sensor 306 to increase the amplitude of the electrical output of the vibration sensor 306. In some embodiments, seismic mass 314 may be omitted.

The male receptacle 304 of the vibration sensor unit 300 or vibration sensor unit 310 can be connected to a female receptacle 302 on a hearing prosthesis (not shown). The female receptacle 302 of the vibration sensor unit 300 or vibration sensor unit 310 can be connected to a male receptacle 304 on the bone-anchored implant in the recipient (not shown). The positions of the male and female receptacles of the vibration sensor unit 300 or vibration sensor unit 310 depend on the configuration of the hearing prosthesis in use by a recipient.

Figure 3C:
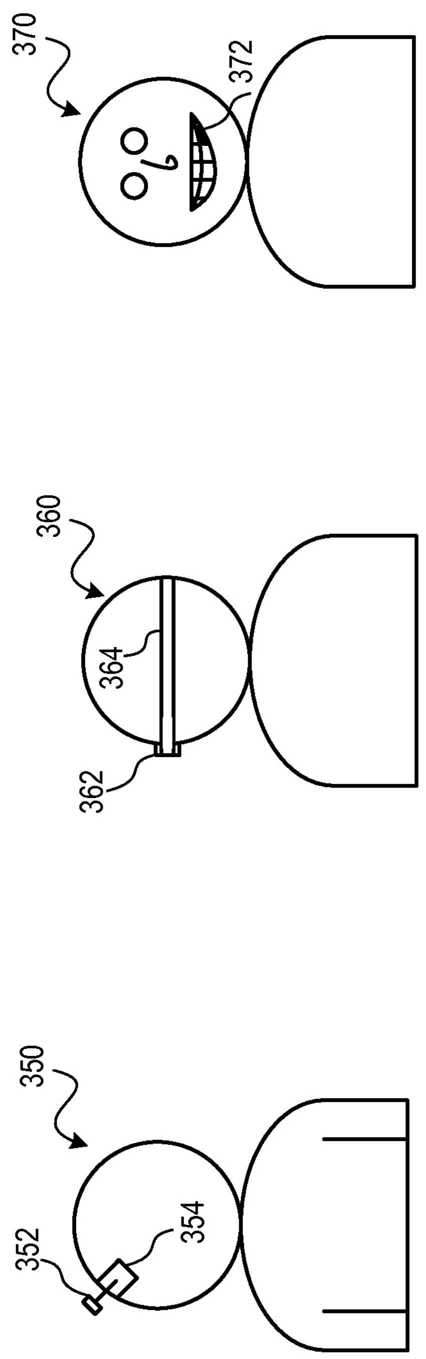
FIG. 3C shows three examples of vibration-based hearing prostheses.

FIG. 3C shows three examples of vibration-based hearing prostheses that can incorporate a vibration sensor similar to those described above with respect to FIG. 3A. In the first example of FIG. 3C, a recipient 350 has a vibration-based hearing prosthesis 352 with a bone-anchored implant 354 implanted in the skull of the recipient 350. In operation, a vibration sensor such as the one shown and described with respect to FIG. 3A can be placed in series between the vibration-based hearing prosthesis 352 and the bone-anchored implant 354.

The second example of FIG. 3C shows a vibration-based hearing prosthesis 362 held in place against the skull of a recipient 360 with an attachment means such as a head band 364. In this example embodiment, either the female receptacle 302 or the male receptacle 304 of the sensor unit 300 of FIG. 3A may be replaced with a physical abutment that physically contacts the skull of the prosthesis recipient 360 to conduct the vibrations from the vibration-based hearing prosthesis 362 to the recipient's skull 360. In operation, a vibration sensor such as the one shown in FIG. 3A can be placed in series between the vibration-based hearing prosthesis 362 and the recipient's skull 360.

Figure 4:
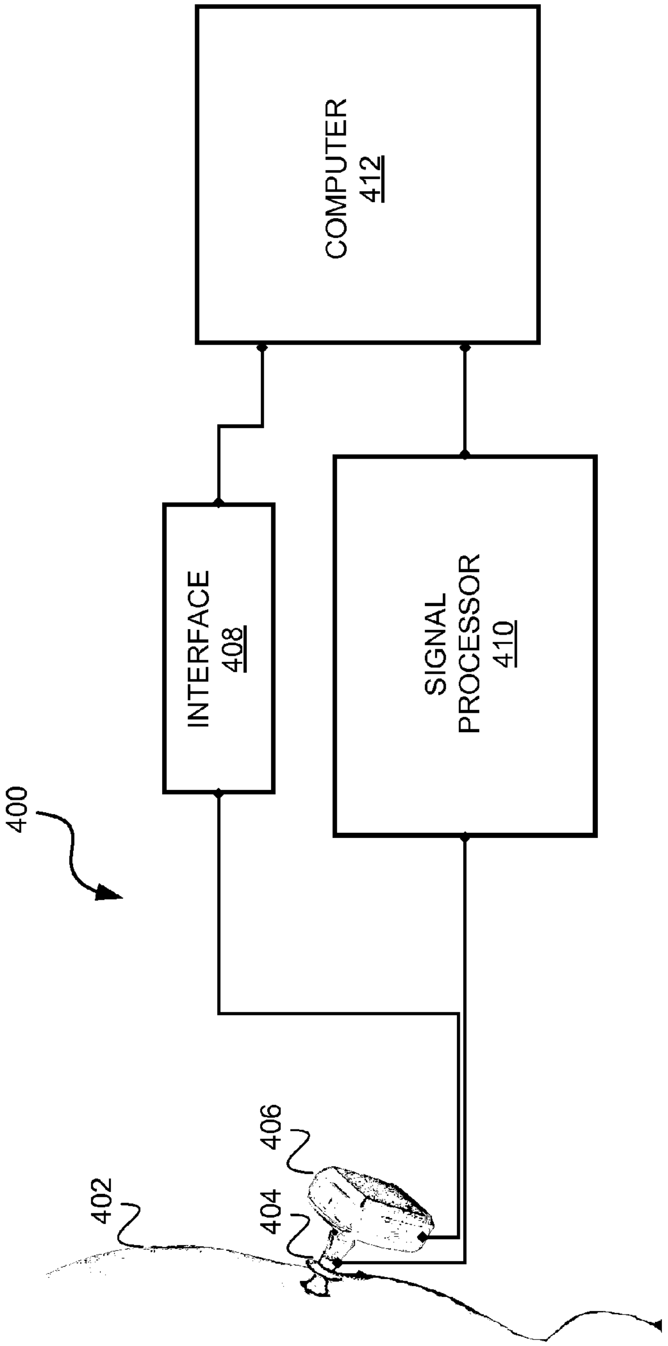
FIG. 4 shows one example hearing prosthesis used in a diagnostic setting.

The third example of FIG. 3C shows a vibration-based hearing prosthesis 372 that is molded to conform to fit one or more of a recipient's 370 teeth. In operation, a vibration sensor such as the one shown and described with respect to FIG. 3A can be placed in series between the vibration-based hearing prosthesis 372 and the one or more teeth of the recipient 370. FIG. 4 shows an example of a hearing prosthesis used in a diagnostic setting. In the diagnostic setting, the methods and apparatuses disclosed herein measure prosthesis stimulus signals in situ. The various functional blocks may be combined into fewer blocks, divided into additional blocks, and/or eliminated based upon the desired implementation. For example, in some embodiments, the interface 408 and the signal processor 410 may be combined into one unit and/or any of components vibration sensor 404, interface 408, and signal processor 410 may be located within the hearing prosthesis 406. Further, the connections between elements may be wired or wireless.

Block diagram 400 includes a vibration-based hearing prosthesis 406 and vibration sensor 404. The hearing prosthesis 406 may be similar to the prostheses 100 or 200 shown and described with respect to FIGS. 1 and 2. In some embodiments, the vibration sensor 404 may be integrated within the hearing prosthesis 406. In operation, the hearing prosthesis 406 receives an acoustic signal, converts the received acoustic signal into a mechanical vibration signal, and applies the mechanical vibration signal to the recipient 402. If the hearing prosthesis is correctly configured, the recipient 402 should perceive the mechanical vibration signal as sound. Because the vibration sensor 404 is in series between the prosthesis 406 and the recipient 402, the vibration sensor 404 can be used to measure or otherwise characterize the mechanical vibration signals generated by the hearing prosthesis 406. Additionally, the hearing prosthesis 406 can be connected to a computer 412 via an interface 408, and the vibration sensor 404 may be connected to the computer 412 through a signal processor 410.

Computer 412 may be a general purpose computer, mobile device, cellular phone, tablet computer, a custom hearing prosthesis device, or other computing device. The interface 408 and the signal processor 410 may connect to the computer via standard computer ports, such as Universal Serial Bus (USB), IEEE 1394, serial port, parallel port, or other port. In some embodiments, the port may be custom designed. In some embodiments, the interface 408 may integrated with the computer 412. The interface 408 is configured to convert signals created by the computer 412 to signals for use by the hearing prosthesis 406, and the interface 408 and the signal processor 410 may be configured to convert signals created by the hearing aid 406 to signals that may be used by the computer 412. For example, the voltage created by the vibration sensor 404 may be buffered and/or amplified by the signal processor 410 for transmission to the computer 412.

The interface 408 connects to the hearing prosthesis 406. The interface 408 enables the computer 412 to communicate with the hearing prosthesis. In some embodiments, the interface 408 may be integrated with either the computer 412 or the hearing prosthesis 406. The computer 412 may send instructions to the hearing prosthesis 406 to perform specific functions. For example, the computer 412 may execute a calibration routine with the hearing prosthesis 406. The interface 408 may allow two way data communication between the hearing prosthesis 406 and the computer 412.

The hearing prosthesis 406 may also provide information about its operation to the computer 412. For example, the hearing prosthesis 406 may provide information relating to a stimulation signal it is currently generating, such as the signal's frequency and amplitude. Additionally, the hearing prosthesis 406 may provide information relating to a stimulus voltage applied to the output signal interface 105 (of FIG. 1). In one embodiment, the computer 412 iteratively varies the parameters of the hearing prosthesis 406. The computer 412 specifies a frequency and amplitude of stimulus for the hearing prosthesis to recreate and provided to the recipient. In one embodiment, the computer 412 contains a database of frequencies and amplitudes associated with a specific prosthesis recipient. For example, the computer starts with a first frequency and gradually increases the amplitude of the output of the hearing prosthesis while the vibration sensor 404 measures the mechanical vibration signal applied by the hearing prosthesis 406 to the recipient 402. The recipient 402 of the hearing prosthesis can indicate when he or she perceives a sound associated with the mechanical vibration signal, thus establishing a hearing threshold associated with the first frequency. The computer 412 then stores the hearing threshold associated with the first frequency in the database.

Once a hearing threshold (along with perhaps other associated parameters) are established for the first frequency, the above-described process may be repeated at a second frequency to establish a hearing threshold associated with the second frequency. The process may be repeated for a plurality of different frequencies across the frequency spectrum of human hearing (or some subset thereof) to establish the recipient's hearing thresholds at different frequencies.

The computer 412 can record different parameters associated with the recipient's hearing threshold. For example, the computer 412 may record the output of the vibration sensor 404. The computer 412 may also record the amplitude of the mechanical vibration signal applied by the hearing prosthesis 406. The recorded amplitude may correspond to a voltage applied to the electromechanical transducer within the hearing prosthesis. Additionally, the computer 412 may calculate an associated stimulus sound pressure level for the hearing threshold. This associated stimulus sound pressure level is the apparent sound pressure level equivalent of the vibration applied to the prosthesis recipient. For example, a vibration that produces an amplitude of 1.5 Volts (V) from the vibration sensor 404 may be equivalent to a sound of 75 decibels sound pressure level (dB SPL) in a human with normal hearing. Thus, the computer may correlate the vibration with an apparent sound pressure level as what a human with normal hearing would hear.

The computer 412 may also run a software application that may assist in configuring the hearing prosthesis 406. For example, the recipient, a technician, an audiologist, or other professional may operate the computer 412 and cause it to execute the computer application. The computer 412 may create or maintain a database that stores parameters associated with the recipient's hearing threshold at different frequencies. The system and methods presented here allow the direct determination of a recipient's hearing threshold directly in situ. By determining a recipient's hearing threshold directly, a hearing prosthesis may be more accurately fitted to a specific recipient.

Additionally, in some embodiments, the computer 412 may be configured to calculate a prosthesis-related transfer function, X(f). For example, the computer 412 can be configured to determine the relationship between the voltage applied to an electromechanical transducer and the vibration conducted to a recipient of the hearing prosthesis. The prosthesis-related transfer function, X(f), is a function of the frequency of the stimulus signal. An example mathematical expression for the transfer function is given below.

$$\text{Vibration}(f)=X(f)*\text{Voltage}(f)$$

Traditionally, a prosthesis-related transfer function is typically calculated based on a human skull simulator. However, because the skull simulator may not accurately reflect the properties of a particular recipient's skull, there may be fitting errors when the hearing prosthesis is fitted to the recipient. The system disclosed herein enables direct measurements of the vibrations conducted to a recipient in situ. Because the calculation of the prosthesis-related transfer function in the disclosed embodiments is based on in situ measurements, a more accurate transfer function may be calculated.

Figure 5:
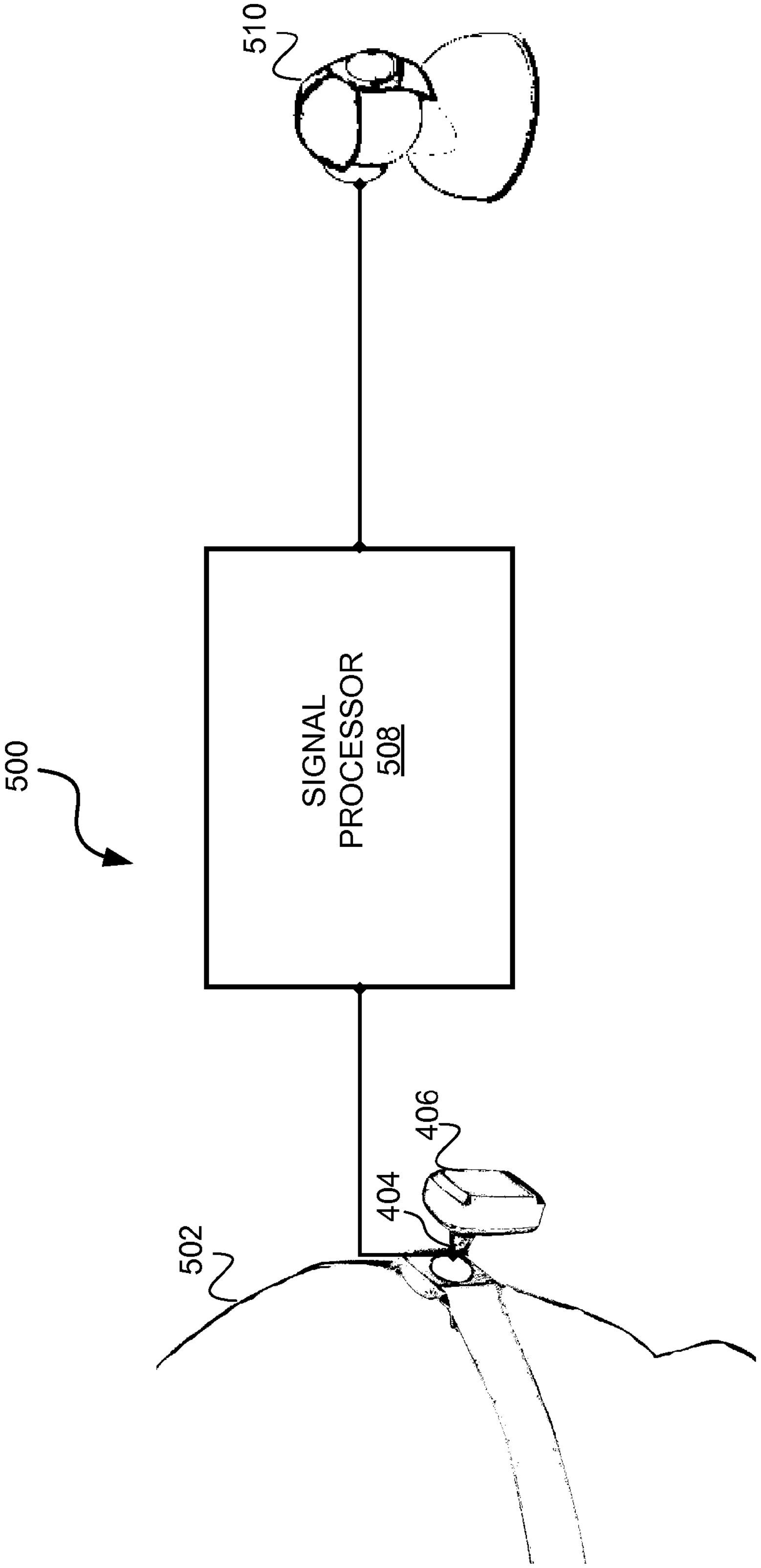
FIG. 5 shows one example hearing prosthesis used in an audio monitoring mode.

FIG. 5 shows one example hearing prosthesis used in an audio monitoring mode. In the audio monitoring mode, the methods and apparatuses disclosed herein enable a third party to monitor, in situ, audio signals conducted to recipient. In some embodiments, the signal processor 508 and/or the vibration sensor 404 may be located within the hearing prosthesis 406. Additionally, the connections between elements may be wired or wireless.

The hearing prosthesis 406 and the vibration sensor 404 shown in FIG. 5 are similar to those described above with respect to the previous figures. The hearing prosthesis 406 and vibration sensor 404 may be integrated the same unit or may be connected together and attached to a recipient 502 according to any of the configurations described herein. In operation, the output of the vibration sensor 404 is connected to a signal processor 508. The signal processor 508 converts the output of the vibration sensor 404 to an acoustic signal for monitoring by another person 510 via a pair of headphones or other form of acoustic speaker system. The signal processor 508 may buffer and amplify the signal from the vibration sensor 404 to create the acoustic signal.

The acoustic signal created by the signal processor 508 can be monitored by a person 510 different from the recipient 502. The person 510 may want to hear the sound corresponding to the vibration signals that are being delivered to the recipient 502, as measured by the vibration sensor 404. For example, if the recipient 502 is a young child or infant, a doctor or parent may wish to monitor audio corresponding to the vibration signals being conducted by the prosthesis 406. The person 510 monitoring the conducted audio signal can assist with system diagnostics.

Some traditional systems may allow monitoring of a signal that is being generated by the hearing prosthesis 406. However, traditional systems do not use a vibration sensor to create the acoustic signal for monitoring of the conducted audio. Thus, traditional systems monitor based on a signal created by a hearing prosthesis rather than the actual vibration signals that are actually conducted to the recipient, as measured by a vibration sensor. These traditional systems may introduce errors into an audio monitoring path. The system disclosed herein enables monitoring of audio conducted to the patient based on the vibrations conducted to a recipient in situ. Because the monitoring of audio in the disclosed embodiments is based on in situ vibrations, the monitored audio is based directly on the audio conducted to recipient.

In one example embodiment, the recipient 502 may not be aware that a vibration signal is being applied; however, the person 510 monitoring would be able to hear a sound corresponding to the vibration signal from the hearing prosthesis 406 based on the output of the vibration sensor 404, thereby enabling person 510 to assist in identifying issues with the hearing prosthesis 406. In another example, a young child may not be able to communicate the fact that he or she is not experiencing a sound sensation in response to a vibration signal applied by the prosthesis 406. However, a visible reaction may be noticed when a vibration signal is applied at an appropriate amplitude. The person 510 assists in monitoring the sound corresponding to the vibration signal applied to the recipient 502, thereby enabling the identification and isolation of system errors.

Additionally, monitoring mode may be used when the electromechanical transducer is turned off, the patient may still be monitored. Sounds made by the body, such as speech, create vibrations in the head as well. The monitoring mode discussed herein allows for other sounds made by the recipient's body to be monitored as well.

Figure 6:
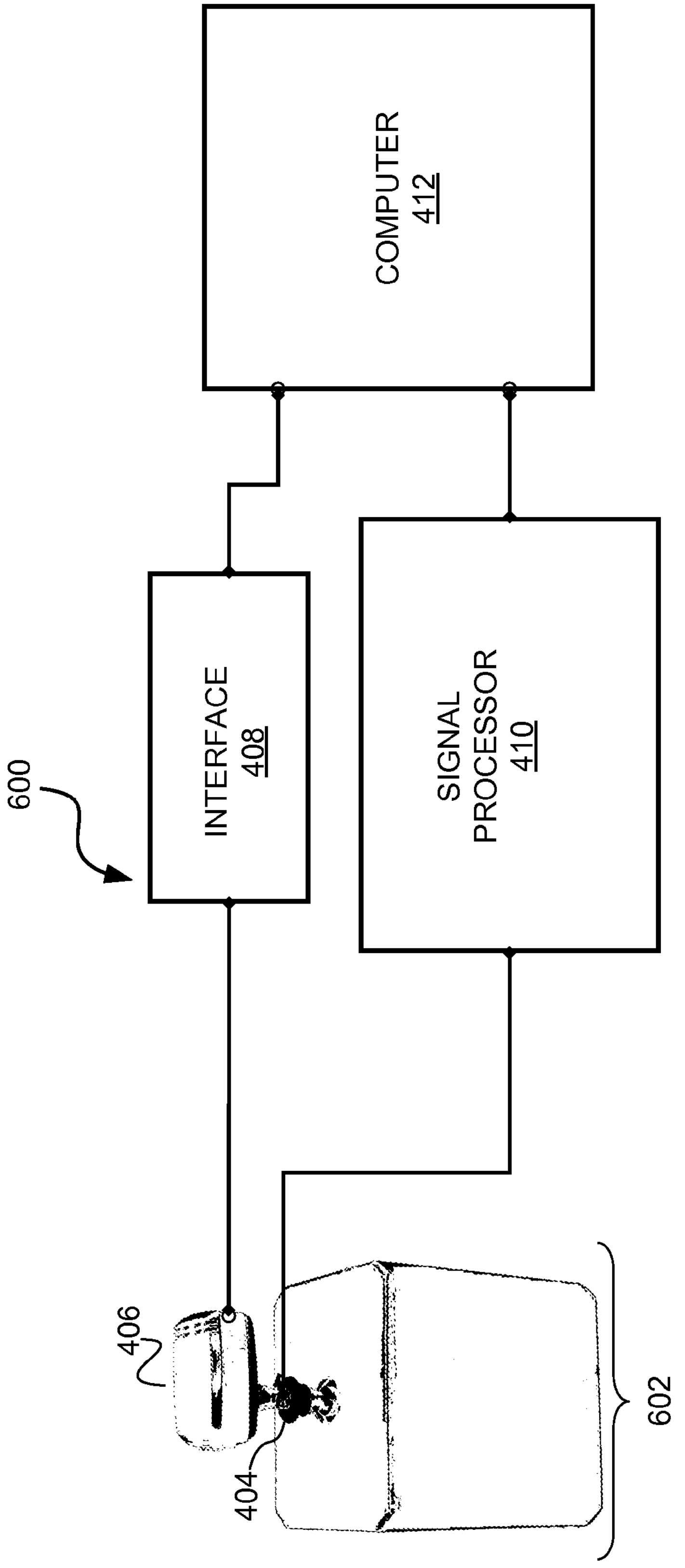
FIG. 6 shows one example hearing prosthesis used in a diagnostic setting.

FIG. 6 shows one example hearing prosthesis used in another diagnostic setting. In the diagnostic setting shown in FIG. 6, the methods and apparatuses disclosed herein can be used to measure vibration stimulus signals. Some aspects shown in block diagram 600 may be performed by the example hearing prosthesis 200 shown in FIG. 2 or other hearing prostheses. Additionally, the hearing prosthesis 100 of FIG. 1 may be used with the diagnostic setting depicted in block diagram 600 as well. The various blocks may be combined into fewer blocks, divided into additional blocks, and/or eliminated based upon the desired implementation. For example, the interface 408 and the signal processor 410 may be integrated into one unit and/or vibration sensor 404 may be integrated within the hearing prosthesis 406. The computer 412, signal processor 410, interface 408, hearing prosthesis 406, and vibration sensor 404 may be similar to or the same as those described with respect to FIG. 4 herein.

Additionally, block diagram 600 includes an impedance load 602. In some embodiments, the impedance load 602 may be skull simulator. A skull simulator attempts to simulate the mechanical impedance that an acoustic signal will encounter when traveling through a human skull. Although a skull simulator may be beneficial for testing a hearing prosthesis, the skull simulator may not exactly emulate the acoustic impedance parameters of the specific recipient's skull. However, the skull simulator can provided valuable information about the hearing prosthesis.

In one embodiment, the computer 412 may iteratively vary the parameters of the hearing prosthesis 406 similar to the method described herein for FIG. 4. The computer 412 may be configured to calculate impedance parameters for a prosthesis recipient relative to the impedance parameters of the impedance load 602. In other embodiments, the impedance parameters for the impedance load 602 may already be known and stored in a database in computer 412. The computer 412 may be configured to run a software application to assist in measuring the impedance load 602. For example, the recipient, a technician, or an audiologist may cause the computer 412 to execute the application and perform the measurements.

The computer 412 may create or maintain a database that stores parameters associated with the impedance load 602 at different frequencies. The computer database can be configured to store parameters associated with both the recipient of the hearing prosthesis 406 as well as parameters of the impedance load 602. In one example, when the computer knows the impedance of the impedance load 602, computer 412 can characterize the electromechanical transducer within hearing prosthesis 406 based on the measurements made with vibration sensor 404.

When the computer 412 knows the impedance parameters associated with the recipient as well as the parameters of the impedance load 602, a recipient-specific calibration can be achieved without the need to attach the hearing prosthesis 406 to the recipient. For example, if a recipient receives a new un-calibrated hearing prosthesis 406, the computer 412 can be used to configure the prosthesis 406 to the specific recipient's head by placing it on the impedance load 602. The computer 412 can cause the hearing prosthesis 406 to create specific stimulation signals and measure the vibration conducted to the impedance load 602 through the vibration sensor 404. Via a mathematical formula, the hearing prosthesis 406 can then be fit to the specific recipient based on the measurements of the impedance load 602. For example, the computer 412 may cause the hearing prosthesis 406 to create a stimulation signal with a known amplitude at a set of predetermined frequencies. When the conducted vibration is measured, it may be compared to known threshold values for the prosthesis recipient. The stimulation amplitude may then be adjusted to make sure the stimulus output will stay above the known threshold values when the prosthesis 406 is connected to the recipient.

Additionally, in another embodiment, the computer 412 transmits parameters to either a doctor or prosthesis manufacturer. The prosthesis 406 is then configured specific to the recipient's head parameters before being delivered to the recipient. Thus, pre-measured in situ measurements of the impedance of a specific recipient's head can be used to more accurately fit a prosthesis 406 to a recipient.

Figure 7:
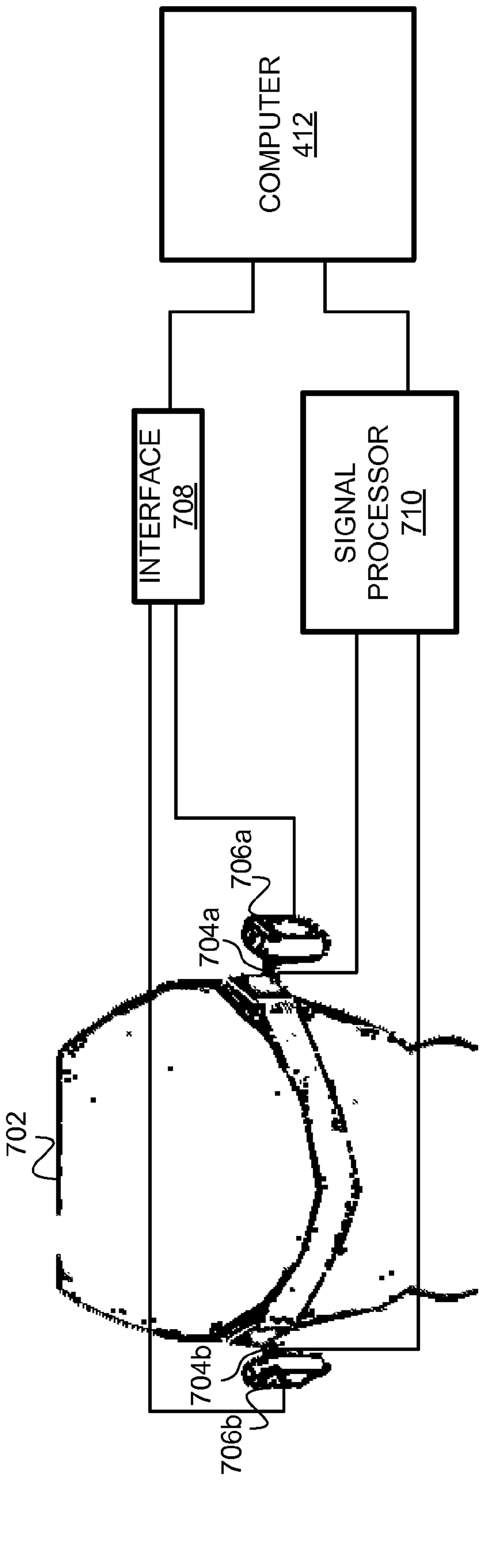
FIG. 7 shows one example two hearing prostheses used in a binaural diagnostic setting.

FIG. 7 shows one example of two hearing prostheses used in a binaural diagnostic setting. In the diagnostic setting, the methods and apparatuses disclosed herein can be used measure prosthesis stimulus signals in situ. Some aspects of block diagram 700 may be performed by the example hearing prosthesis 200 shown in FIG. 2 or other hearing prostheses. Additionally, the hearing prosthesis 100 of FIG. 1 may be used with block diagram 700 as well. The various blocks may be combined into fewer blocks, divided into additional blocks, and/or eliminated based upon the desired implementation. For example, the interface 708 and the signal processor 710 may be integrated into one unit and/or each vibration sensor **704*a* and 704*b* may be integrated within each hearing prostheses 706*a* and 706*b*, respectively. The computer 412, signal processor 710, interface 708, hearing prostheses 706*a* and 706*b*, and vibration sensors 704*a* and 704*b* may be similar to or the same as those described with respect to FIG. 4** herein.

The methods and apparatuses described herein allow both hearing prostheses **706*a* and 706*b* to be measured at the same time. This binaural (both ear) fitting allows crosstalk between hearing prostheses 706*a* and 706*b* to be measured. In one embodiment, the computer 412 may iteratively vary the parameters of one of the hearing prosthesis 706*a* or 706*b* similar to the procedure described herein for FIG. 4**.

For example, a first vibration signal may be applied to the recipient 702 by the first hearing prosthesis **706*a* located near the recipient's 702 right ear. Both the vibration sensor 704*a* near the right ear and the vibration sensor 704*b* near the left ear may measure the first vibration signal applied to the recipient 702 by the first hearing prosthesis 706*a*. Because the second hearing prosthesis 706*b* would not be creating a vibration signal at the same time, any vibration signal measured by the second hearing prosthesis 706*b* would have been conducted through the recipient's 702** head.

Thus, the computer 412 may also be configured to calculate a head-related transfer function from the first hearing prosthesis **706*a* to the second hearing prosthesis 706*b*. The head-related transfer function is a function of the frequency, amplitude, and phase of the vibration signal applied to the recipient 702 of the first hearing prosthesis. The head-related transfer function gives the relationship between the vibrations measured at one vibration sensor associated with one hearing prosthesis with the vibrations applied to the recipient 702** by the opposite hearing prosthesis. Thus, the head-related transfer function is a measure of the vibration that has propagated from one side of a recipient's head to the other side of the head.

The equations below show two head-related transfer functions, $H_{21}(f,A,\phi)$ and $H_{12}(f,A,\phi)$. The function $H_{21}(f,A,\phi)$ relates the vibration applied to the recipient 702 of the second prosthesis **706*b* and measured with measured at the second vibration sensor 706*a* with the vibration measured at the first vibration sensor 704*a*. Similarly, $H_{12}(f,A,\phi)$ relates the vibration applied to the recipient 702 of the first prosthesis 706*a* and measured with measured at the first vibration sensor 704*a* with the vibration measured at the second vibration sensor 704*b***.

$$\text{Vibration}_1(f,A,\phi)=H_{12}(f,A,\phi)*\text{Vibration}_2(f,A,\phi)$$

$$\text{Vibration}_2(f,A,\phi)=H_{21}(f,A,\phi)*\text{Vibration}_1(f,A,\phi)$$

The head-related transfer function in this example is also known as cross talk. In one embodiment, once both head-related transfer functions, $H_{21}(f)$ and, $H_{12}(f)$ may be minimized after each is measured, thus reducing cross talk. For example, cross talk may be minimized by applying a patient specific inverse filter based on the measured head-related transfer function. In some systems with multiple hearing prostheses, cross talk is undesirable. The methods disclosed herein allow measurements to be made in situ that enable a calculation of parameters specific to the individual recipient of the hearing prosthesis to identify and ameliorate the undesirable effects of crosstalk. Additionally, in some embodiments cross talk may be desirable. In these cases, the head-related transfer functions may be used to calculate a filter to maximize constructive interference caused by the cross talk.

Figure 8:
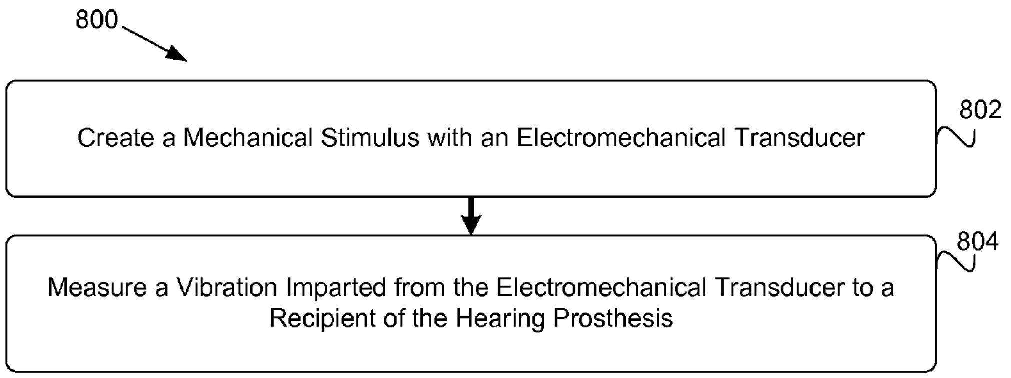
FIG. 8 shows one example method for use with the hearing prosthesis disclosed herein.

FIG. 8 shows one example method for use with the embodiments disclosed herein. Method 800 begins with block 802. At block 802, a mechanical stimulus (e.g., a mechanical vibration signal) is created with an electromechanical transducer. The electromechanical transducer is a part of a hearing prosthesis. In one embodiment, the mechanical stimulus is based at least in part on an acoustic signal received by a microphone associated with the hearing prosthesis. In another embodiment, the mechanical stimulus is based at least in part on an audio signal created by the hearing prosthesis, such as a tone or chirp.

In one embodiment, the mechanical stimulus (e.g. a mechanical vibration signal) is applied to the recipient's skull via a physical implant (e.g., a bone-anchored implant) connected to the recipient's skull. In other embodiments, the mechanical stimulus may be applied to the prosthesis recipient by placing the electromechanical transducer of the hearing prosthesis directly against the recipient's head. For example, the recipient may wear a headband with the hearing prosthesis. The headband may hold the electromechanical transducer of the hearing prosthesis in a position to apply the vibration directly the recipient's skull. In another embodiment, the prosthesis may fit around a recipient's teeth, and the mechanical stimulus may be applied directly to the recipient's teeth.

At block 804, the mechanical stimulus applied to the skull of the recipient is measured according to any of the methods and procedures disclosed herein. In operation, a vibration sensor is configured to measure the amplitude and frequency of the mechanical stimulus applied by the electromechanical transducer of the hearing prosthesis to either (i) the prosthesis recipient's skull or (ii) an impedance load as described herein.

The detailed description disclosed herein describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

For illustration purposes, some features and functions are described with respect to bone anchored hearing apparatuses, such as the Cochlear™ Baha®. However, many features and functions may be equally applicable to other types of hearing prostheses. Certain aspects of the disclosed systems, methods, and articles of manufacture could be applicable to any type of hearing prosthesis now known or later developed.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A hearing prosthesis comprising:

a first mechanical actuator configured to generate a first mechanical vibration signal based at least in part on a first electrical signal, and to apply the first mechanical vibration signal to a recipient of the hearing prosthesis, wherein the first electrical signal has a frequency and an amplitude; and a first vibration sensor configured to directly measure the first mechanical vibration signal applied by the first mechanical actuator to the recipient of the hearing prosthesis, wherein the first vibration sensor is located in series between the first mechanical actuator and the recipient of the hearing prosthesis.

2. The hearing prosthesis of claim 1 wherein the first vibration sensor is a piezo-electric element.

3. The hearing prosthesis of claim 1 wherein the first vibration sensor is a piezo-resistive element.

4. The hearing prosthesis of claim 1 further comprising a seismic mass, wherein the seismic mass is coupled to the first vibration sensor and is configured to tune the first vibration sensor to adjust an output of the first vibration sensor.

5. The hearing prosthesis of claim 1 further comprising an enclosure, wherein the first mechanical actuator and first vibration sensor are located within the enclosure.

6. The hearing prosthesis of claim 1 further comprising:

a first coupling unit configured to connect the first mechanical actuator to the first vibration sensor; and a second coupling unit configured to connect the first vibration sensor to the recipient of the hearing prosthesis.

7. The hearing prosthesis of claim 1 wherein the first vibration sensor is further configured to measure a second mechanical vibration signal transmitted from a second mechanical actuator, wherein the second mechanical vibration signal has a frequency and an amplitude based at least in part on a second electrical signal, and wherein the second mechanical actuator is associated with a second hearing prosthesis for the recipient.

8. The hearing prosthesis of claim 7 further comprising the second hearing prosthesis including a second vibration sensor, wherein:

the second vibration sensor is further configured to measure the first mechanical vibration signal; and the second vibration sensor is further configured to measure the second mechanical vibration signal.

9. The hearing prosthesis of claim 1 wherein the frequency of the first electrical signal is iteratively adjusted.

10. The hearing prosthesis of claim 1 wherein the amplitude of the first electrical signal is iteratively adjusted.

11. The hearing prosthesis of claim 1 further comprising output circuitry and an acoustic speaker, wherein the output circuitry is configured to create a signal for the acoustic speaker based at least in part on the first mechanical vibration signal measured by the first vibration sensor.

12. A method comprising:

creating a first mechanical stimulus with a first electromechanical transducer associated with a hearing prosthesis, wherein the first mechanical stimulus is based at least in part on an electrical signal that has an amplitude and a frequency;

measuring the first mechanical stimulus imparted from the first electromechanical transducer to a recipient of the hearing prosthesis, wherein measuring the first mechanical stimulus includes directly measuring the first mechanical stimulus with a first mechanical stimulus sensor; and determining, using a processor coupled to the first mechanical stimulus sensor, and based at least in part on the measured first mechanical stimulus, a recipient's hearing threshold associated with the frequency of the electrical signal.

13. The method of claim 12 further comprising creating an acoustic output based on the measured first mechanical stimulus, and applying the acoustic output to an acoustic speaker.

14. The method of claim 12 further comprising varying the amplitude of the electrical signal.

15. The method of claim 12 further comprising measuring a second mechanical stimulus with the first mechanical stimulus sensor, wherein the second mechanical stimulus is imparted from a second electromechanical transducer to the recipient of the hearing prosthesis, wherein the second electromechanical transducer is associated with a second hearing prosthesis.

16. The method of claim 15 further comprising calculating a head transfer function based at least in part on the measured second mechanical stimulus.

17. The method of claim 12 further comprising measuring a stimulus voltage associated with the recipient's hearing threshold.

18. The method of claim 17 further comprising calculating a transfer function for the hearing prosthesis.

19. The method of claim 12 further comprising calculating an associated stimulus sound pressure level for the hearing threshold.

20. The method of claim 12 wherein the first mechanical stimulus sensor is external to the recipient.

21. A method comprising:

measuring an acoustic signal with a microphone associated with a hearing prosthesis; creating a stimulation signal based on the measured acoustic signal;

applying the stimulation signal to a transducer, wherein the transducer converts the stimulation signal to a mechanical vibration;

outputting the mechanical vibration to a hearing prosthesis recipient; and measuring the mechanical vibration with a vibration sensor mechanically coupled to the hearing prosthesis recipient, wherein the vibration sensor is located in series between the transducer and the recipient of the hearing prosthesis so that measuring the mechanical vibration includes the vibration sensor directly measuring the mechanical vibration.

22. The method of claim 21 further comprising varying an amplitude of the stimulation signal.

23. The method of claim 22 further comprising determining a hearing threshold based at least in part on the measured mechanical vibration.

24. The method of claim 21 further comprising calculating a transfer function for the hearing prosthesis.

25. The method of claim 21 wherein the vibration sensor is external to the recipient.

26. A hearing prosthesis system comprising:

a hearing prosthesis that includes a transducer and a first coupling means, wherein the transducer is configured to generate a vibration signal based on an electrical signal, wherein the electrical signal has a frequency and an amplitude, and wherein the first coupling means is configured to conduct the vibration signal from the transducer to a recipient of the hearing prosthesis; and a sensor unit that is external to the hearing prosthesis, wherein the sensor unit is configured to measure the vibration signal conducted by the first coupling means, wherein the sensor unit further includes second coupling means configured to conduct the vibration signal from the transducer through the sensor unit to the recipient.

27. The hearing prosthesis of claim 26 further comprising a seismic mass, wherein the seismic mass is coupled to the sensor unit and is configured to tune the sensor unit to adjust an output of the sensor unit.

28. The hearing prosthesis of claim 26 further comprising an enclosure, wherein the transducer is located within the enclosure and the sensor unit is located outside the enclosure.

* * * * *